Figure 1:
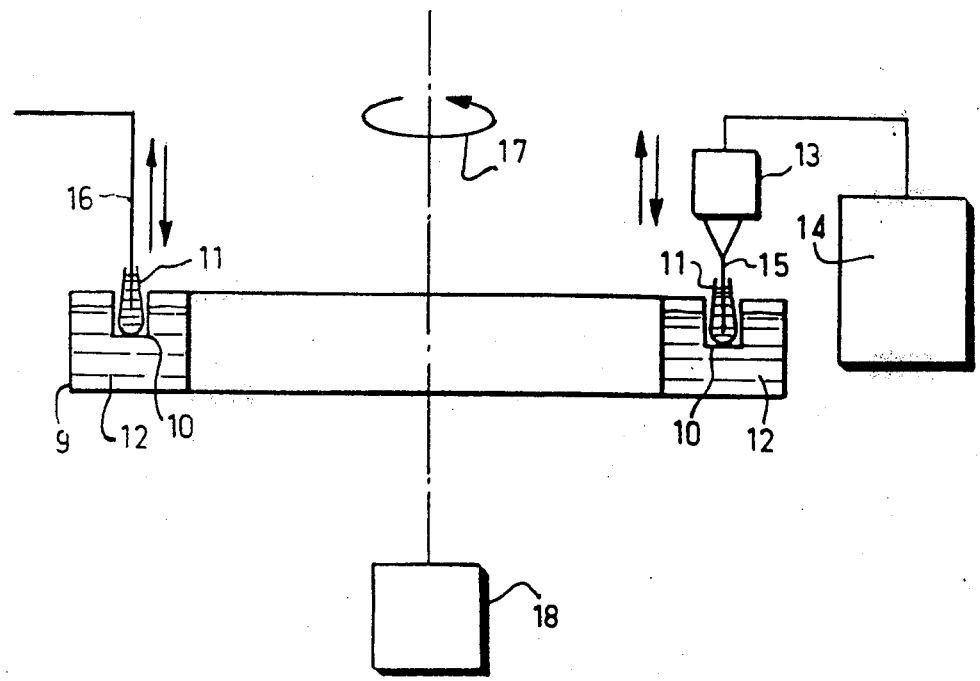

United States Patent [19]

Thivend et al.

[11] 4,188,466

[45] Feb. 12, 1980

[54] AUTOMATIC METHOD FOR THE DETERMINATION OF STARCH

[75] Inventors: Pierre Thivend, Romagnat; Christiane Mercier-Greenwood, Antony; André Guilbot, Nantes, all of France

[73] Assignee: I.N.R.A., Paris, France

[21] Appl. No.: 813,275

[22] Filed: Jul. 6, 1977

[30] Foreign Application Priority Data

Jul. 7, 1976 [FR] France ............................. 76 21361

[51] Int. Cl.$^2$ ..................... C12D 13/02; G01N 31/14
[52] U.S. Cl. ........................................ 435/18; 435/96; 435/288; 435/291; 435/803; 435/808; 435/813
[58] Field of Search ............. 195/127, 103.5 R, 51 R; 23/230 R, 230 A, 253 R, 230 M

[56] References Cited

U.S. PATENT DOCUMENTS

| 3,720,583 | 3/1973 | Fisher | 193/31 R |
|---|---|---|---|
| 3,826,615 | 7/1974 | Smythe et al. | 23/230 R |
| 3,937,615 | 2/1976 | Clack et al. | 23/253 R |
| 4,049,381 | 9/1977 | Burns et al. | 23/230 R |
| 4,116,631 | 9/1978 | Trinel | 195/103.5 M |

OTHER PUBLICATIONS

Meuser, "Accuracy of the Enzymic Determination of Glucose", *Chem. Abstracts*, vol. 77, No. 13, p. 308 (1972) Abs. No. 86703f.

Gracza, "Minor Constituents of Starch", *Starch Chemistry and Technology*, vol. 1, Whistler et al., ed. (1965), Academic Press, N.Y., p. 122.

*Primary Examiner*—Thomas G. Wiseman
*Attorney, Agent, or Firm*—Michael Ebert

[57] ABSTRACT

A method and system for the automatic determination of the weight of starch or similar substances in various forms of simple or complex substrates. In a system in accordance with the invention, dispersion of starch is effected by ultrasonics and enzymatic hydrolysis is carried out continuously in segmented form. The colorimetric determination of glucose obtained thereby is also effected continuously in segmented form.

12 Claims, 5 Drawing Figures

AUTOMATIC METHOD FOR THE DETERMINATION OF STARCH

BACKGROUND OF INVENTION

This invention relates to a method and system for automatically determining the weight of starch or similar substances in various forms of simple or complex substrates.

The quantitative analysis of starch in various substrates is required for different reasons. First of all, amylaceous substances constitute one of the principal sources of energy in animal and human food; hence there is a strong interest in starch determination for nutritional studies. Secondly, those industries which use or convert starch and amylaceous products always have a need for methods to carry out quantitative analysis of these substances. Thirdly, the market value of certain products such as bran depends directly on their starch weight content, and this, too, is responsible for an interest in methods for starch determination.

Throughout the entire specification, it is to be understood that by "starch" is meant either any solid colloid insoluble in cold water having the chemical formula $(C_6H_{10}O_5)_n$ or $[C_6(H_2O)_5]_n$ which is chemically identical to any polymer of glucose containing $\alpha 1 \to 4$ and/or $\alpha 1 \to 6$ and/or $\alpha 1 \to 3$ linkages, whatever its origin, whether animal or vegetable, and whatever its customary name—for instance, glycogen, fecula or tapioca—or any similar product derived directly from the starch defined above—for instance, dextrins and oligoholosides. Starch, as defined above, can be a substantially pure substance (starches from wheat, corn, casara, potato, etc.) or it can be part of more complex media (for instance, grains, vegetables, oil cakes, composite feeds, etc.).

A manual method for the rapid and specific analysis of starch in different amylaceous substrates has already been proposed. This known method involves the following steps:

Step 1: If the treated sample of the substrate to be analyzed is not already in particulate form, the material must first be divided into particles, as by crushing. In general, the particles obtained should have a particle diameter of 1 mm, or less than 0.5 mm.

Step 2: A particulate sample (for instance 0.5 g), or a test sample having the particle size stipulated above—that is to say, a diameter less than 1 mm or 0.5 mm—is suspended in a suitable aqueous medium (for instance, 25 ml of water purified by ion-exchange treatment), and the starch contained in the form of grains in the particles of the sample is dispersed in the medium. These two operations are generally carried out hydrothermally, and more specifically by "starching"; that is, by bringing the mixture of aqueous medium and particulate sample to a boil for about 3 minutes and then autoclaving the latter (140° C. and 2.5 kg/cm$^2$) for about 1 hour. In this way, there is obtained a dispersion of starch in the aqueous medium.

Step 3: All or an aliquot portion of the starch dispersion is hydrolyzed enzymatically with the use of an enzymatic hydrolysis preparation comprising at least glucoamylase (coming from strains of Rhizopus delmar or Aspergillus niger) in order to convert the dispersed starch quantitatively into D-glucose, dissolved in the aqueous dispersion medium. For this purpose, the aqueous medium comprises a buffer solution (for instance, acetic acid buffer, 2-M sodium acetate) in order to bring the hydrolysis pH to between 4 and 5, and a bactericidal agent (for example, sodium ethyl mercury thiosalicylate, also known as sodium merthiolate) which is capable of inhibiting the development of any microorganism. The hydrolysis is carried out with continuous agitation at a temperature close to 50°0 to 60° C. for about 5 hours. The concentration by weight of the enzymatic preparation relative to the weight of the sample of substrate analyzed varies, depending on the origin and degree of purity of the hydrolysis enzyme. In general, it is between 10 and 20%, which corresponds on the average to about 150 I.U. of glucoamylase for 0.5 g of starch. A hydrolysate is thus obtained.

Step 4: From the hydrolysate, a glucose solution is prepared containing a predetermined portion, in the present case all of the glucose resulting from the hydrolysis of the starch. For this purpose, the hydrolysate is filtered with a folded paper filter and the insoluble solid residue collected on the filter is washed quantitatively, so that the filtrate obtained constitutes the desired glucose solution.

Step 5: A weight determination of the glucose contained in the glucose solution is then effected, from which there is deducted the starch content by weight of the substrate analyzed.

For this purpose, one proceeds by enzymatic and colorimetric means, first of all by oxidizing the glucose in aqueous and/or alcoholic phase so as to form gluconic acid, with liberation of hydrogen peroxide due to the catalytic action of an enzyme; namely, glucose-oxydase. Secondly, by reacting the hydrogen peroxide thus liberated with a hydrogen-donor chromogenic agent—namely, orthodianisidine—with the generation of a coloring substance due to the catalytic action of another enzyme; namely, peroxydase. Thirdly, by blocking the two reactions defined above either with hydrochloric acid, in which case one obtains a yellow color, or with sulfuric acid, in which case one obtains a pink color. The optical density of the color thus obtained, which is proportional to the amount of glucose, is then measured, from which one deduces the starch content by weight of the substrate analyzed.

The action of these enzymes is enhanced by a pH of the order of 7.2, corresponding to the introduction into the reaction medium of a buffer having a base of trihydroxymethylaminomethane, also known as TRIS buffer. The two reactions defined above require a period of time of about 45 minutes, a temperature of about 20° C., and complete darkness in order to develop.

When a complete substrate contains, in addition to the starch, glucose and/or oligoholosides and/or dextrines and/or glucides capable of liberating glucose under the action of glucoamylase, the above-described analytical method does not make it possible to distinguish and determine these different substances separately. If one desires to analyze them separately, it is then necessary to have recourse to one of the following additional preliminary operations:

(a) If one wishes to determine solely the starch content, it is then necessary, prior to the dispersion (Step 1) described above in aqueous medium, to proceed with an aqueous and/or alcoholic extraction (40% alcohol) to eliminate dextrines and/or glucides and/or oligoholosides. The determination of the starch content is then carried out on the residue.

(b) If one desires to determine starch plus dextrines, it is then necessary, before the dispersion (1) described above in aqueous medium, to carry out an alcoholic extraction (80% alcohol) in order to eliminate the glucose and the other oligoholosides.

For more details concerning the method defined above and different variants thereof, reference may be had to the following publications:

(1) Article entitled "Determination of Starch in Complex Media" by P. Thivend, C. Mercier and A. Guilbot, pp. 513-526, vol. 5 (4) of the *Annales de Biologic animale, Biochimie, Biophysique of* 1965.

(2) Article entitled "Determination of Starch with Glucoamylase" by P. Thivend, C. Mercier and A. Guilbot, pp. 100-105, Vol. VI, of the book having the general title *Methods in Carbohydrate Chemistry,* edited by R. L. Whistler, Academic Press (New York and London).

(3) Article entitled "Use of Glucose Amylase for the Determination of Starch" by P. Thivend, C. Mercier and A. Guilbot, pp. 278-283, issue 9 of the 17th year of the 1965 book having the general title *"Der Stärke"* (Wissenschaftliche Verlagagesellschaft M.B.H., Stuttgart).

(4) Publication entitled "The Enzymatic Determination of Starch in Dietary Foods" by H. Ruttloff, M. Rothe, R. Freise and R. Schierbaum, pp. 201-212, Vol. 130, issue 4 of the 1966 journal entitled *Zeitschrift fur Lebensmitteln Untersuchen und Forschnung.*

(5) Article by E. Y. C. Lee and W. J. Whelan, published in 1966 in the *Archives of Biochemistry and Biophysics,* Vol. 116, p. 162.

(6) Article by M. L. Salo and M. Salmi, entitled "Determination of starch by the amyloglucosidase method" published in 1968 in the *Journal of the Scientific Agricultural Society of Finland,* pp. 38-45, Vol. 40.

(7) Article by J. C. Macrae, D. C. Armstrong, entitled "Enzymatic method for determination of α-linkage glucose polymers in biological materials" published in 1968, pp. 578-581, Vol. 19, *Journal of Science and Food Agriculture.*

(8) Article by I. F. Ebeli, published on page 25 of Vol. 8, 1969, of *Phytochemistry.*

(9) Article by F. Meuser and W. Kempf, entitled "Analytical Problems and Possible Uses of Enzymatic Starch Determination," published in 1970, Vol. 22, 12 (pp. 417-423) of *Die Stärke.*

(10) Article by R. A. Libby, entitled "Direct Starch Analysis using DMSO Solubilization and Glucoamylase," published in 1970, pp. 473-481, Vol. 47 of *Cereal Chemistry.*

(11) Article by R. F. H. Dekker and G. N. Richards, entitled "Determination of Starch in Plant Material," published in 1971, pp. 441-444, Vol. 22, *Journal of Science and Food Agriculture.*

All the articles mentioned above are incorporated by reference in the present specification.

Though the method of analysis described above has made it possible extensively to simplify the determination of starch, it nevertheless is still relatively lengthy. In practice, it is not feasible to determine more than 12 samples per day under the usual conditions which prevail in an analytical laboratory. This is due essentially to the fact that the operations of:

dispersing the starch of a particulate sample in an aqueous medium by "starching" and autoclaving,
enzymatic hydrolysis,
preparation of the glucose solution necessary for the titration, by filtration, remain essentially manual operations; that is to say, each of them requires one or more personal actions to carry out.

Under these circumstances, automating the above-described prior art method of starch determination appears to be impossible. Yet there is an ever increasing need for methods which make it possible automatically to carry out a large number of serial determinations of starch content.

SUMMARY OF INVENTION

In view of the foregoing, it is the main object of the present invention to so modify all or part of the operating steps 1 to 4, in the above-described manual method, in order to provide a method of starch determination that lends itself to at least partial, if not complete, automation, without essentially changing the method employed and without modifying its underlying principles.

For this purpose, in order of importance is the operating step 3 involving enzymatic hydrolysis. This constitutes the most significant step of the present method of starch determination; for the accuracy of the method depends on its efficiency—that is to say, on the rate of conversion of the starch into glucose.

In order to open the door to automation of this operating step, it is necessary to replace the batch technique of enzymatic hydrolysis in the prior art manual method by a continuous technique of hydrolysis, and more particularly by a suitable tubular flow of the mixture during hydrolysis, one end of which corresponds to the mixture of the dispersion of starch and enzymatic hydrolysis preparation to be hydrolyzed, and the other end of which corresponds to said hydrolyzed mixture. But then, the man skilled in the art is immediately confronted by the following difficulties:

(1) The mixture to be hydrolyzed comprises, in particular, an aqueous medium, the starch dispersed therein, and the enzymatic preparation. One is thus confronted with essentially a suspension of heterogeneous particles of a solid which is insoluble in an aqueous medium. Under these circumstances, any flow of the mixture to be hydrolyzed is capable of giving rise to a heterogeneity in behavior of the solid phase as compared with that of the liquid phase, particularly at different respective speeds of flow of these two phases. An incomplete hydrolysis of the starch may then result, due to local or complete modification of the enzyme/substrate weight ratio for a given time of hydrolysis, corresponding to a predetermined time of passage in a hydrolysis enclosure.

(2) The hydrolysis must be carried out with agitation in order to homogenize the flow during hydrolysis. Since the cross-section of any flow of the mixture to be hydrolyzed remains relatively small, in view of the fact that the volume of the test sample is always limited, it is practically impossible to provide effective agitation in a stream of small cross-section.

(3) The particles suspended in the continuous flow during hydrolysis may at any moment obstruct the tubular flow conduit or conduits for the hydrolyzed mixture.

(4) A priori, no generally or especially known fact permits a man skilled in the art to conclude that a continuous enzymatic hydrolysis of starch, carried out in tubular flow, can be complete.

In the light of these four factors, no solution appears, a priori, satisfactory for effecting the enzymatic hydrolysis in question continuously with tubular flow.

However, due to the experimental record reported below and the test results obtained therefrom, it has been discovered in accordance with the present invention that it was possible to carry out continuously the operation of enzymatic hydrolysis of a starch dispersion, provided that:

A. A segmented flow of the mixture of the starch dispersion and the enzymatic hydrolysis preparation is formed; that is to say, a flow comprising at least one composite fluid vein including at least one segment of said mixture, limited on both sides by two gas plugs, respectively.

B. The segmented flow thus formed is caused to circulate in a hydrolysis enclosure for a period of time sufficient to convert the starch dispersed in the aqueous medium of a segment, such as defined previously, into glucose dissolved in said aqueous medium.

It has also been discovered that only segmentation of the mixture to be hydrolyzed by a suitable segmentation gaseous phase makes it possible to limit the volume—that is to say, essentially, the length of the sample to be hydrolyzed—and therefore promotes at each segment a proper homogenization of the mixture to be hydrolyzed as well as a complete hydrolysis of the starch treated.

Furthermore, the hydrolysis operating procedure in accordance with the invention makes it possible successively to separate different samples of different substrates to be analyzed respectively, and therefore lends itself effectively to the automatic performance of serial analyses.

Moreover, the method of hydrolysis in accordance with the invention can now be carried out with certain automatic determination lines available on the market, which are well known to those skilled in automatic analysis. In particular, these lines employ proportioning pumps as well as peristaltic pumps, described, in part or in whole, in the following patents:

U.S. Pat. Nos. 3,134,263; 3,241,432; 3,227,091; 3,306,229 and 3,425,357;

French Pat. Nos. 2,107,507; 2,107,093 and 2,107,509.

The following information will make it possible to specify different operating conditions which must be satisfied in order to be able satisfactorily to effect automatic hydrolysis in accordance with the present invention with the automatic determination lines previously mentioned.

In the manual method previously described, step 2 for the dispersion of the starch has heretofore been effected by "starching" and autoclaving. Such a method of dispersion undeniably constitutes an obstacle to automating the method of determination in accordance with the invention and it is unfortunately not possible to carry out this operating step continuously.

However, in accordance with the present invention, due to experimental studies the results of which are reported below, a method of dispersing starch has been discovered which differs from the prior technique and can easily be included in an automatic analysis line. This dispersion method entails the use of ultrasonic energy to act in a known manner on a particulate sample suspended in the aqueous dispersion medium while maintaining the suspension of the particulate sample at a temperature between about 90° C. and about 100° C. (preferably between about 90° C. and about 95° C.).

This novel method of dispersing starch has proved to be superior even to the prior purely hydrothermal method to the extent that the action of the ultrasonics on the dispersion makes it possible to avoid any gelatinization of the starch and therefore any deposit on the bottom of the treatment container.

Finally, with regard to operating step 4—namely, the preparation of the glucose solution necessary for the titration of the starch—by means of the experiments reported below we have discovered that automating the method of determination is made possible in accordance with the invention by a dialysis technique; that is to say:

(1) By forming a first segmented flow of the hydrolysate, comprising at least one composite fluid vein containing at least one segment of the said hydrolysate, limited on both sides by two gas plugs, respectively;

(2) By forming a second segmented flow of a counter-dialysis solution comprising at least one composite fluid vein containing at least one segment of the said counter-dialysis solution, limited on both sides by two gas plugs, respectively;

(3) By causing the first segmented flow and the second segmented flow to circulate in the same direction on either side of a dialysis wall, in which manner, by at least partial diffusion of glucose from a segment of the hydrolysate towards a segment of the counter-dialysis solution, there is obtained on the one hand a segmented flow of the hydrolysate which is at least partially depleted of glucose, and on the other hand a segmented flow of a glucose solution.

OUTLINE OF DRAWINGS

Figure 2C:
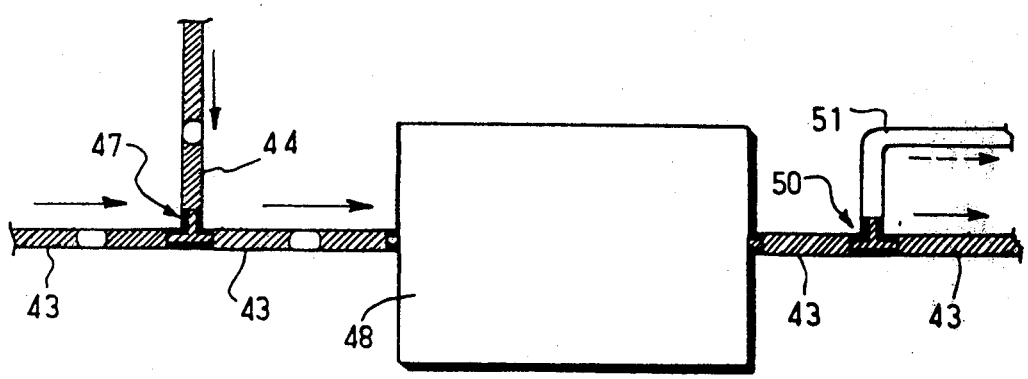
Figure 2:
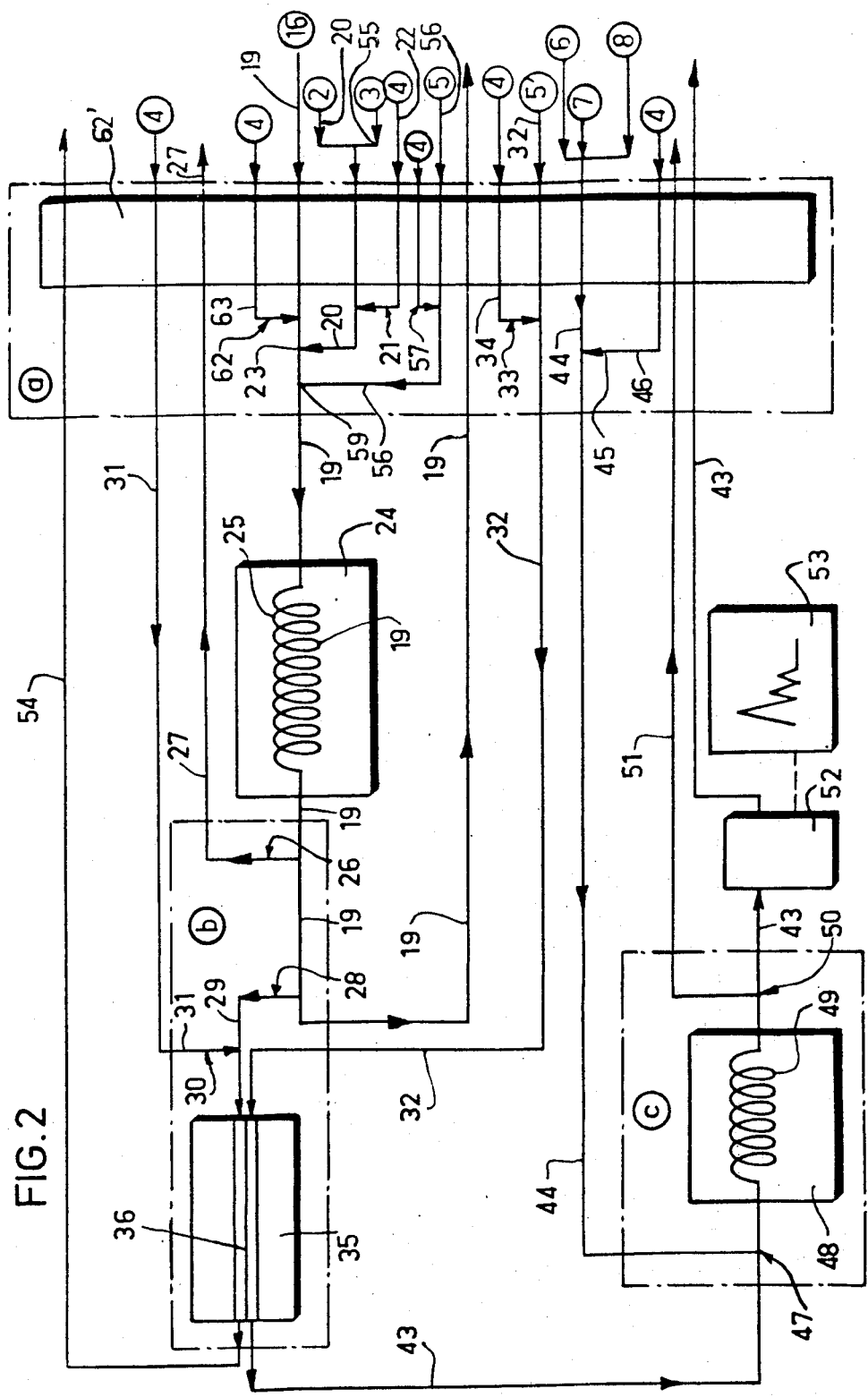
Figure 2A:
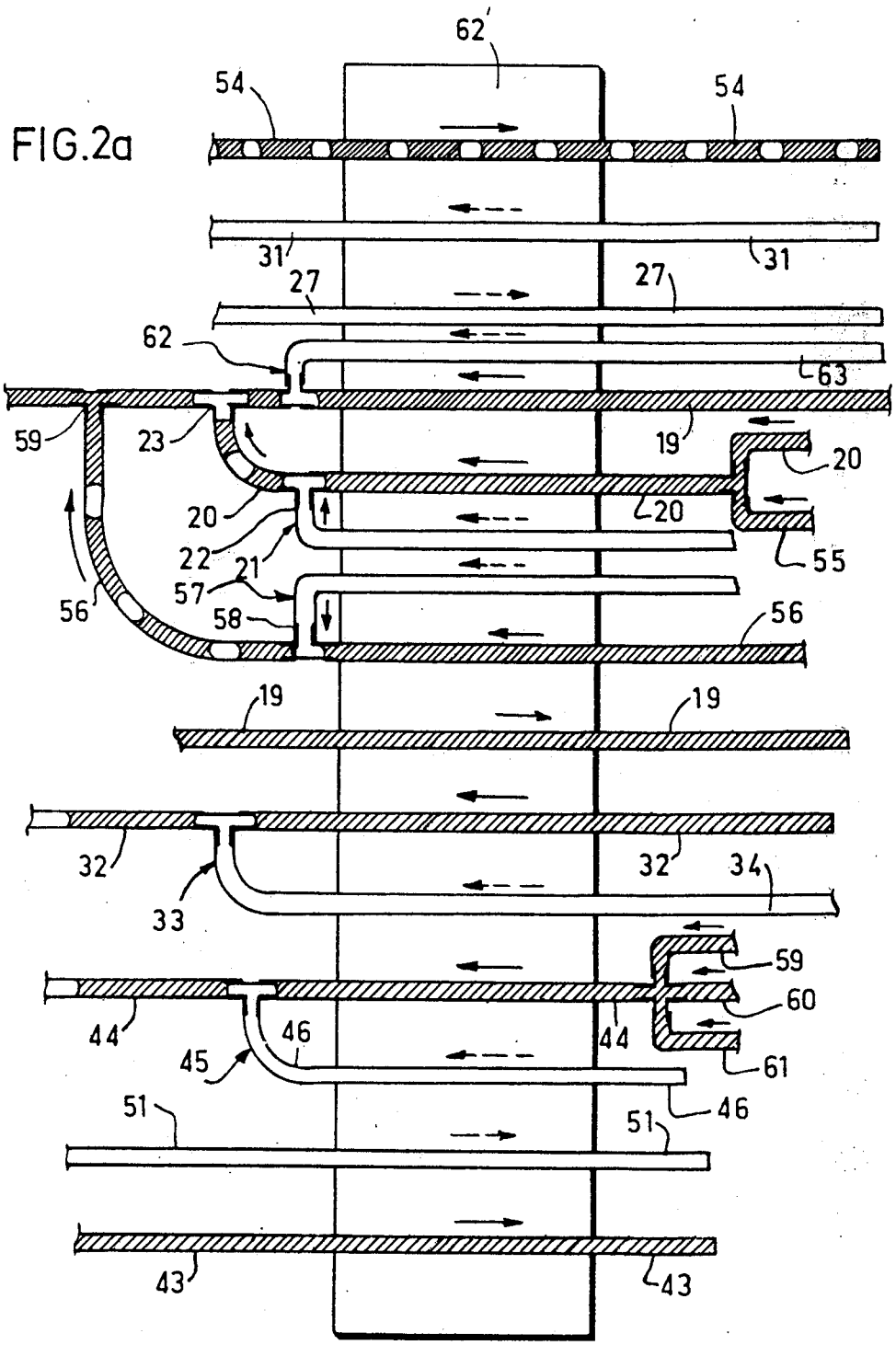
Figure 2B:
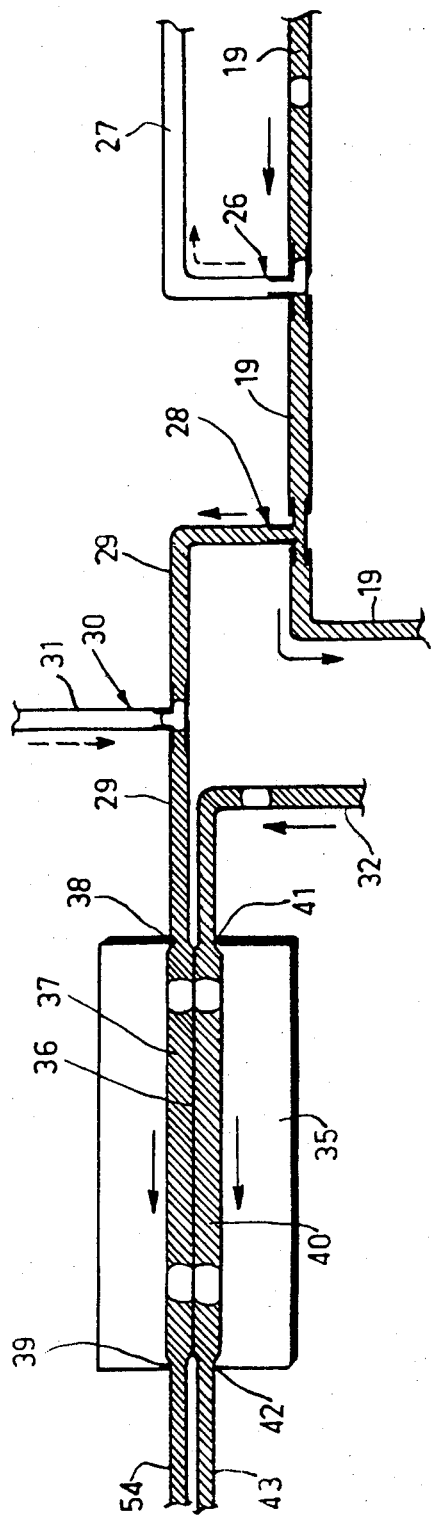

For a better understanding of the invention as well as other objects and further features thereof, reference is made to the following detailed description to be read in conjunction with the accompanying drawings, wherein:

FIG. 1 schematically illustrates an apparatus in accordance with the invention for treating particulate samples of substrate suspended in an aqueous medium by means of ultrasonic energy; and FIG. 2 shows an automatic determination system or line in accordance with the invention, three different sections of this line being shown in FIGS. 2a, 2b and 2c.

DESCRIPTION OF INVENTION

An automatic starch determination system in accordance with the present invention comprises (1) a treatment apparatus of the type illustrated in FIG. 1 which makes it possible to treat different particulate samples of amylaceous substrate suspended in an aqueous medium and by ultrasonic action to disperse in the medium the starch contained in the particles of said substrate, (2) an automatic analysis line as illustrated in FIGS. 2a, 2b and 2c.

Referring to FIG. 1, the treatment apparatus in accordance with the invention comprises the following components:

A. A turntable 9 provided with a plurality of compartments 10 adapted to receive a plurality of flasks 11. Each flask contains a sample of a material to be treated—namely, an amylaceous substrate to be analyzed—suspended in an aqueous medium. Compartments 10 are regularly distributed in a circle on the turntable 9;

B. Means 12 for heating the samples, fixedly attached to the turntable 9, making it possible to maintain the plurality of compartments 10 at a suitably selected predetermined temperature, for instance 94° C. As shown in FIG. 1, heating means 12 consists of a water bath in which compartments 10 are at least partly immersed;

C. A vertically movable ultrasonic probe 13 at a position corresponding to that of compartments 10 on turntable 9. Probe 13, which is coupled to an ultrasonic generator 14, includes an extension 15 having the shape of a rod which is dipped temporarily into each treatment flask 11;

D. A vertically movable device 16 for sampling the different samples treated, the position of device 16 corresponding to that of compartments 10 on turntable 9. Device 16 is spaced angularly, for instance by 180°, with respect to ultrasonic probe 13. More precisely, for a given sample, device 16 is located behind probe 13 as seen in the direction of rotation of turntable 9 represented by the arrow 17;

E. Means for periodically rotating turntable 9, indicated symbolically by block 18;

F. Means to effect vertical displacement of ultrasonic probe 13 and sampling device 16, synchronized with rotating means 18;

G. Means (not shown) for washing extension 15 of ultrasonic probe 13 with hot water.

The operation of the treatment apparatus shown in FIG. 1 is as follows:

One: Ultrasonic probe 13 and sampling device 16 are in their lowered position; that is to say, they are immersed in suspensions contained in two treatment flasks 11 in alignment with probe 13 and device 16, respectively. One of the samples is then treated by ultrasonics, while the sample which is 180° away is withdrawn towards the analysis line represented in FIG. 2.

Two: Ultrasonic probe 13 is then rinsed by means of hot water (not shown), whereupon probe 13 and device 16 are brought into raised position.

Three: Then turntable 9 is indexed one notch, bringing two new treatment flasks into a position in alignment with probe 15 and sampling device 16, respectively.

Four: Probe 13 and device 16 are then again lowered and immersed in suspensions contained in the two new flasks, and a new treatment is commenced in which the above steps are repeated, and so on.

Obviously, in an apparatus as shown in FIG. 1, ultrasonic probe 13 can be arranged alongside of sampling device 16, the sequence of steps being otherwise the same.

As shown in FIGS. 2, 2a to 2c, an automatic determination line in accordance with the present invention comprises the following elements.

Element 1: A first segmented flow means or conduit 19 for a starch dispersion coming from sampling device 16. Conduit 19 consists of a sized tube of small cross-section of compressible, flexible plastic material, making it possible to assure a flow of a composite fluid vein (see 2a) comprising at least a segment of the dispersion in question, limited on both sides by two gas plugs, respectively.

Element 2: A second flow means or conduit 20 for an enzymatic hydrolysis preparation 2, including at least glucoamylase. Conduit 20 consists of a sized tube of small cross-section of compressible, flexible plastic which permits a flow of a liquid vein (see FIG. 2a) of the enzymatic preparation in question.

Element 3: A first segmentation means 21 for the flow of the enzymatic hydrolysis preparation 2. First means 21 comprises a third conduit 22 (sized tube of small cross-section of compressible flexible plastic), connected to the second conduit 20 for the flow of a gaseous vein (air coming from a source 4) (see FIG. 2a).

More specifically, segmentation means 21 permits the periodic introduction into the liquid vein of the second conduit 20 of the gas plugs (see FIG. 2a) on either side of the liquid components of the enzymatic preparation 2.

Element 4: A first means 23 for combining the segmented flow of the starch dispersion coming from the sampling device 16 with the segmented flow of the enzymatic hydrolysis preparation 2, the first means 23 being located downstream of the first segmentation means 21, as seen in the direction of flow of the enzymatic hydrolysis preparation 2. The first combining means 23 consists of the combination of first conduit 19 and of second conduit 20, which have been defined above.

Element 5: A hydrolysis enclosure 24, within which there is arranged horizontally a portion of the first flow conduit 19 having the shape of a coil 25. This enclosure 24 consists of a thermostatically-controlled box, maintained for instance at 55° C., located downstream of the first combining means 23, as seen in the direction of flow of the segmented mixture of the starch dispersion (coming from sampling device 16) and the enzymatic hydrolysis preparation 2.

Element 6: A first desegmentation means 26 for the hydrolyzed mixture of the starch dispersion and the enzymatic preparation. This first means 26 is located downstream of hydrolysis enclosure 24, as seen in the direction of flow of said mixture. First means 26 comprises a fourth sized conduit 27 of small cross-section of compressible, flexible plastic material, connected to the first conduit 19 for the flow of a gaseous vein (see FIGS. 2a and 2b). First desegmentation means 26 makes it possible to break up the composite fluid vein (see FIG. 2b) of the first conduit 19 into the gaseous vein, formed of the different gas plugs of the composite fluid vein in question, and a non-segmented vein of the hydrolyzed mixture, formed of the different segments of the composite fluid vein in question.

Element 7: A settling means 28 located downstream of the first desegmentation means 26 (as seen in the direction of flow of the hydrolyzed mixture), permitting the separation from the unsegmented vein of hydrolyzed mixture obtained in the manner previously indicated of the relatively fine particles of the solid residue which is insoluble in the aqueous medium of the hydrolyzed mixture in question. Settling means 28 comprises a fifth conduit 29 (sized tube of small cross-section of compressible, flexible plastic material), connected substantially vertically to the first conduit 19, itself arranged substantially horizontally. Fifth conduit 29 is then intended for the flow of a non-segmented hydrolysate vein containing the relatively fine particles of the solid residue in question.

Element 8: A resegmentation means 30 for the hydrolysate flow previously obtained, located downstream of the settling means 28, as seen in the direction of flow of the unsegmented hydrolysate vein. Means 30 comprises a sixth conduit 31 or sized tube of small cross-section of compressible, flexible plastic material, connected to fifth conduit 29, for the flow of a gaseous vein (air 4) (see FIGS. 2a and 2b). Resegmentation means 30 makes it possible periodically to introduce (see FIG. 2b) into the hydrolysate vein of fifth conduit 29 gas plugs on both sides of the two hydrolysate segments.

Element 9: A third flow means for a counter-dialysis saline solution 5', consisting of a seventh conduit 32 or sized tube of small cross-section, of compressible, flexible plastic material, for the flow of the liquid vein (see FIG. 2a) of solution 5'.

Element 10: A second means 33 for the segmentation of the flow of saline solution 5, consisting of an eighth conduit 34 or sized tube of small cross-section of compressible, flexible plastic material, connected to seventh conduit 32. Eighth conduit 34 communicates with the open air 4, and permits the flow of a gaseous vein; as previously, the second segmentation means 33 makes it possible periodically to introduce (see FIG. 2a) into the liquid vein of seventh conduit 32, gas plugs on both sides of liquid segments.

Element 11: A dialysis cell 35, comprising on opposite sides of a dialysis wall 36 (see FIG. 2b), a first compartment 37 on one side provided with a first inlet 38, connected to fifth conduit 29, for the segmented flow of the hydrolysate which is at least partially depleted of glucose, and a second compartment 40 on the other side provided with a second inlet 41, connected to seventh conduit 32, for the segmented flow of the counter-dialysis solution, and a second outlet 42 for a segmented flow of a glucose solution. The two inlets 38 and 41 of dialysis cell 35 are located on the same side of the latter, while the two outlets 39 and 42 are located on the opposite side.

Element 12: A fourth segmented flow means for the glucose solution previously obtained, consisting of a ninth conduit 43 or sized tube of small cross-section of compressible, flexible plastic connected to the second outlet 42 of dialysis cell 35. Ninth conduit 43 permits a flow of a composite fluid vein of the glucose solution.

Element 13: A fifth flow means for a reactive solution comprising, in particular, an enzymatic coloring preparation 6, a chromogenic agent 7, and possibly a buffer 8. This flow means consists of a tenth conduit 44, or sized tube, of small cross-section of compressible flexible plastic material, conduit 44 permitting a flow of a liquid vein of the reactive solution previously defined.

Element 14: A third means 45 for segmenting the flow of the reactive solution, comprising an eleventh conduit 46 leading to the open air 4, consisting of a sized tube of small cross-section, of compressible plastic material. This tenth conduit 46 permits the flow of a gaseous vein, and the segmentation means 45 in its turn makes it possible periodically to introduce into the liquid vein of tenth conduit 44 gas plugs on the two sides of the liquid segments.

Element 15: A second means 47 for combining the segmented flow of the glucose solution and the segmented flow of the reactive solution. This second means 47 is located downstream of third segmentation means 45, as seen in the direction of flow of the reactive solution. The second means 47 in question consists of the combination of ninth conduit 43 and tenth conduit 44.

Element 16: A reaction enclosure 48 within which there is arranged a coil-shaped portion 49 of the fourth flow means (ninth conduit 43). This enclosure 48 consists of a thermostatically-controlled box maintained, for instance, at 37° C., located downstream of the second combining means 47, as seen in the direction of segmented flow of the glucose solution.

Element 17: A second desegmentation means 50 for the chromogenic mixture which has reacted within the reaction enclosure 48, located downstream of the latter as seen in the direction of flow of the mixture in question. The second desegmentation means 50 comprises a 12th conduit 51, or sized tube, of small cross-section of compressible, flexible plastic material, connected with ninth conduit 43. The 12th conduit 51 permits the flow of a gaseous vein, and the second desegmentation means 50 in its turn makes it possible to decompose the composite liquid vein of ninth conduit 43 into the gaseous vein defined previously, consisting of the different gas plugs of fluid vein 43, which is discharged through conduit 51, and into a non-segmented colored liquid vein formed of the different segments of fluid vein 43.

Element 18: A colorimeter 52 connected to a recorder 53, which makes it possible to measure and record the optical density of the color of the unsegmented colored liquid vein flowing after desegmentation in conduit 43.

Element 19: A 13th conduit 54 connected to the first outlet 39 of the dialysis cell 35, permitting the evacuation of the segmented flow of hydrolysate, which is at least partially depleted in glucose. As previously, conduit 54 is a sized tube of small cross-section of flexible, compressible plastic material.

Element 20: A 14th conduit 55 for the flow of a liquid vein of a buffer 3, connected to the inlet of second conduit 20. As previously, conduit 55 is a sized tube of small cross-section, of compressible plastic material.

Element 21: Possibly, a 15th conduit 56 for the flow of a liquid vein of a diluent; for instance, distilled water 5. As previously, conduit 56 is a sized tube of small cross-section of flexible, compressible plastic.

Element 22: Possibly, a fourth means 47 for the segmentation of the flow of the diluent, comprising, as previously, a 16th conduit 58 (see FIG. 2a) opening into the open air 4 and connected to 15th conduit 56. The 4th segmentation means 57 makes it possible periodically to introduce into the flow of diluent flowing in 15th conduit 56, gas plugs on opposite sides of liquid segments.

Element 23: Possibly, a third combining means 59, consisting of the combining of 15th conduit 56 and first conduit 19, downstream of the first combining means 23, as seen in the direction of flow of the mixture to be hydrolyzed, which makes it possible to dilute the latter.

Element 24: A 17th conduit 59, connected to a source 6 of enzymatic coloring preparation, an 18th conduit 60 connected to a source 7 of a chromogenic agent, possibly a 19th conduit 61 connected to a source 8 of a suitable buffer. All the conduits 59, 60 and 61 (sized tubes of small section of compressible, flexible plastic material) are connected to the inlet of the fifth flow means, consisting of tenth conduit 44 described above, and serving for the flow of the reactive coloring solution.

Element 25: A fifth segmenting means 62 for the flow of the starch dispersion coming from sampling device 16 of FIG. 1. This fifth means 62 comprises a 20th conduit 63 opening into the open air 4 and connected to first conduit 19. Fifth means 62 makes it possible periodically to introduce into the flow of the starch dispersion circulating in conduit 19, gas plugs on both sides of dispersion segments.

Element 26: A peristaltic proportioning pump, represented diagrammatically by box 62', connected with all the conduits of small cross-section 54, 31, 27, 63, 19, 20, 22, 58, 56, 34, 32, 44, 46, 51, and 43; in the manner known, per se, and, for instance, as described in U.S. Pat. Nos. 3,306,229 and 2,935,028. The peristaltic pumps contemplated by the present invention consist very generally in a series of pressing cylinders which periodically come into contact with the flexible tubes described above and move along them a certain distance before leaving them.

The segmentation means 21, 33, 45, and possibly 57, and the resegmentation means 30 which have been described above can, in pratice, be controlled by any suitable device which makes it possible to maintain the length of the segments and the length of the gas plugs constant. For this purpose, one may, for instance, use a pressing rod device which makes it possible to compress the corresponding gas flow conduits against a suitable cushion and to close off the conduits at precise moments which are controlled by the movement of the pressing cylinders of the peristaltic pump (see, for instance, U.S. Pat. Nos. 3,306,229 and 3,425,357). Furthermore, it is not necessary that gas flow conduits 63, 22, 58, 34, 46 and 31 be connected with the peristaltic pump. As a matter of fact, in place of the latter, a source of compressed air or any other suitable segmentation gas can be employed.

As shown in FIG. 2a, peristaltic pump 62' (circulating means for the fluids) makes it possible to cause the different fluids to circulate; in particular, in the first flow means (first conduit 19), in the second flow means (second conduit 20), possibly in the first segmentation means 21 (third conduit 22), in the first combining means 23, possibly in the hydrolysis enclosure 24, in the resegmentation means 30, in seventh conduit 32, possibly in eighth conduit 34, in tenth conduit 44, possibly in 11th conduit 46, and 20th conduit 63.

The method of procedure for the automatic determination of starch in accordance with the invention comprises the following steps:

(1) If the substrate to be analyzed is not already in particulate form, or if the substrate is not divided with sufficient fineness, one, first of all, divides the substance to be analyzed into particles by any suitable means, such as by crushing. In general, the crushing effected must be sufficient to obtain particles of a diameter less than or equal to 0.4 mm, for the reasons indicated hereinbelow.

(2) A particulate sample—for example, 500 mg of the substance having the particle size stipulated above—is placed in suspension in a suitable aqueous medium; for instance, in 50 ml of distilled water, contained in a treatment flask 11.

(3) By arranging the treatment flask or flasks 11 in compartments 10 of turntable 9, which are reserved for this purpose, as shown in FIG. 1, the starch contained in the particles of each of the treated samples is dispersed in the aqueous suspension medium by the action of ultrasonics. For this purpose, the temperature of the water bath 12 is regulated in such a manner that each suspension of particulate sample is maintained at a temperature close to 94° C., for the reasons indicated above. At the same time, the periodic rotating means 18 is governed, in synchronism with ultrasonic probe 13 and sampling device 16, in such a manner that ultrasonic probe 13 treats each particulate sample in suspension for about 4 minutes (including the time of rinsing of probe 13), for the reasons indicated hereinbelow. By way of example, the frequency of ultrasonic generator 14 is 20 kilocycles per second, and its electric power is 150 W.

(4) Due to the fifth segmenting means 62 and by means of the first conduit 19, a segmented flow of the dispersion of starch sampled by device 16 in FIG. 1 is formed. Due to the first segmented means 21 and by means of second conduit 20, there is established a segmented flow of the enzymatic hydrolysis preparation 2 (comprising glucoamylase) and the selected buffer 3 (for instance, acetic acid buffer, 2 M sodium acetate). Due to the first combining means 23, the segmented flow of the starch dispersion coming from the sampling device 16 of FIG. 1 is combined with the segmented flow of the enzymatic hydrolysis preparation 2 and selected buffer 3. Due to the fourth segmenting means 57, and by means of 15th conduit 56, a segmented flow of a suitable diluent—for instance, distilled water—is possibly formed. Due possibly to the third combining means 59 arranged downstream of the first combining means 23, as seen in the direction of segmented flow of the starch dispersion, a segmented flow is formed of the mixture to be hydrolyzed proper, comprising, therefore, the starch dispersion sampled by device 16, possibly the selected diluent 5, the enzymatic hydrolysis preparation 2, and the selected buffer 3. As from the third combining means 23, one therefore has a segmented flow of the mixture to be hydrolyzed and, more precisely, of a composite fluid vein comprising a plurality of segments of the mixture to be hydrolyzed, each limited on opposite sides by two gas plugs, respectively. The adjustment of the analysis line is such that, on the one hand, at the place of the first combining means 23, a segment of the enzymatic preparation and of the selected buffer is combined with a segment of the starch dispersion and not with a gaseous plug, and, on the other hand, possibly at the location of the third combining means 59, a segment of the diluent combines with a segment of the mixture of the starch dispersion, the enzymatic preparation, and the selected buffer. Moreover, as a function of the concentration of the enzymatic hydrolysis preparation 2 and that of the selected buffer 3, the volume of each segment flowing in conduit 20 and/or the volume of each segment possibly flowing in conduit 56, and/or the volume of each segment flowing in conduit 19, upstream of the first combining means 23, are selected in such a manner that each segment of the mixture to be hydrolyzed, circulating downstream of the third combining means 59, has, on the one hand, a weight ratio of the enzymatic preparation 2, with respect to the weight of the particulate sample of substrate analyzed contained in the same segment of the mixture to be hydrolyzed, which is close to about 7 (for the reasons indicated below) and, on the other hand, a concentration of selected buffer of close to 1/10 M.

(5) The segmented flow of the mixture to be hydrolyzed is caused to flow downstream of the third combining means 59 into coil 25 arranged in the hydrolysis enclosure 24, which is thermostatically-controlled at 55° C., for instance. The time of circulation of the mixture to be hydrolyzed is sufficient to transform the starch dispersed in the aqueous medium of one segment into glucose dissolved in said medium. By way of example, the hydrolysis time—that is to say, the time of flow in coil 25—is close to about 1 hour.

(6) Due to the first desegmentation means 26 and by means of the first conduit 19, the flow of the hydrolyzed mixture is desegmented downstream of hydrolysis coil 25 and therefore of the hydrolysis enclosure 24. More precisely, due to the fourth conduit 27 and the first conduit 19, the composite fluid vein of the hydrolyzed mixture is decomposed, on the one hand, into a gaseous stream formed of the different gas plugs of the composite fluid vein in question, circulating in conduit 27, and on the other hand, into a non-segmented stream of hydrolyzed mixture, formed of the different segments of the same composite fluid vein, circulating in conduit 19, downstream of the first desegmentation means 26.

(7) Due to settling means 28—that is to say, due to the juncture of the fifth vertical conduit 29 and the first horizontal conduit 19—the relatively fine particles of the solid residue which is insoluble in the aqueous medium of the hydrolyzed mixture are separated from the unsegmented stream flowing in conduit 19, downstream of the desegmentation means 26. Stated differently, due to the means 28, the relatively fine particles are separated by gravity from the relatively coarse particles of the solid residue in question which is insoluble in the aqueous medium of the hydrolyzed mixture. More precisely, the non-segmented stream circulating downstream of the first desegmentation means 26 is separated, on the one hand, into a first non-segmented flow containing the relatively fine particles of the solid residue circulating in the fifth conduit 29 and, on the other hand, into a second non-segmented flow containing the relatively coarse particles of the same solid residue, circulating in the rest of conduit 19, downstream of settling means 28.

(8) Due to the resegmentation means 30 and by means of the fifth conduit 29, the flow of the hydrolysate is resegmented. More precisely, from the first non-segmented flow circulating in the fifth conduit 29 and from the gaseous stream circulating in the sixth conduit 31, there is reformed a composite fluid vein, downstream of the resegmenting means 30, comprising a plurality of hydrolysate segments, each limited on its two sides by gas plugs. There is thus formed a new segmented flow of the hydrolysate, hereinafter referred to as the first flow.

(9) Due to the second segmentation means 33 and by means of the seventh conduit 32, a second segmented flow of a saline counter-dialysis solution 5' is formed, and therefore a composite fluid vein comprising a plurality of segments of the saline solution selected, limited on its two sides by two gas plugs.

(10) In the dialysis cell 35, there is circulated, in parallel flow, on opposite sides of the dialysis wall 36, the first segmented flow, introduced through the first inlet 38, and the second segmented flow, introduced through the second inlet 41. In this way, by at least partial diffusion of glucose from a segment of the hydrolysate circulating in the first compartment 37 towards the segment of the counter-dialysis solution circulating in the second compartment 40, there is obtained, on the one hand, a segmented flow of the hydrolysate which is at least partially exhausted of glucose, evacuated through the first outlet 39 and, on the other hand, a segmented flow of a glucose solution, discharged through the second outlet 42. The adjustment of the automatic analysis line is effected in such a manner that, within dialysis cell 35, a segment of the hydrolysate has the same length as that of a segment of the counter-dialysis solution, on the one hand, and, on the other hand, a segment of the hydrolysate circulates in coincidence with the segment of the counter-dialysis solution (see FIG. 2b).

(11) Due to the third segmentation means 45 and by means of the tenth conduit 44, a segmented flow is formed of a reactive solution circulating in conduit 44 downstream of the third segmentation means 45; this reactive solution comprises the enzymatic coloring preparation 6 (comprising glucose-oxydase and peroxydase), the selected chromogenic agent 7 (for instance, orthodianisidine), and the selected buffer 8 (for instance, trihydroxymethylaminomethane). Therefore, downstream of the third segmentation means 45, there is a composite fluid vein comprising a plurality of segments of the previously defined reactive solution, bounded on both sides by gas plugs.

(12) Due to the second combining means 47, the segmented flow of said reactive solution circulating in the tenth conduit 44 is combined with the segmented flow of the glucose solution circulating in the ninth conduit 43, the latter being connected to the second outlet 42 of hydrolysis cell 35. Downstream of combining means 47 and upstream of the reaction enclosure 48, there is thus a segmented flow of a chromogenic mixture comprising the glucose solution circulating in conduit 43, the enzymatic coloring preparation 6, the chromogenic agent 7, and buffer 8. As a consequence, upstream of enclosure 48, there is a composite fluid vein comprising a plurality of segments of said chromogenic mixture, bounded on two sides by two gas plugs. Regulation of the automatic analysis chain is effected in such a manner that, at the location of the second combining means 47, a segment of the reactive solution circulating in conduit 44 combines with a segment of the glucose solution circulating in conduit 43, and not with a gas plug. By way of example, the enzymatic coloring preparation 6, the chromogenic agent 7, and buffer 8 are available in the form of a single reaction mixture, obtained from a solution of 60 g/l of trihydroxymethylaminomethane, the pH of which is brought to 7.3 with about 40 ml/l of pure hydrochloric acid, and by dissolving in the solution thus obtained about 2 g/l of glucose oxydase (Type 2, marketed by the American SIGMA Company), about 10 mg/l of peroxydase (Type 2, marketed by SIGMA), and about 150 mg/l of orthodianisidine.

(13) The segmented flow of chromogenic mixture is circulated, downstream of the combination point 47, into the reaction enclosure 48, and more precisely into coil 49, at a temperature of, for instance, close to 37° C., for a period of time sufficient to convert the chromogenic agent dissolved in a segment of the mixture circulating in coil 49 into a coloring substance. By way of example, the time of circulation of such a segment of coil 49—that is to say, the reaction time in the latter—is close to 45 minutes.

(14) At the outlet of the reaction enclosure 48—that is to say, at the outlet of coil 49, due to the second desegmentation means 50, and by means of the ninth conduit 43—the flow of the reactor chromogenic mixture circulating in conduit 43 is desegmented. More precisely, due to conduits 43 and 51, the composite fluid vein emerging from the reaction enclosure 43 is broken down, on the one hand, into a gaseous stream circulating in the 12th conduit 51 formed of the different gas plugs of the composite fluid view in question and, on the other hand, into a non-segmented liquid stream of the reacted chromogenic mixture circulating in the ninth conduit 43 downstream of the second desegmentation means 50, formed of the different segments of the fluid vein in question.

(15) By means of colorimeter 52 and recorder 53, the optical density of the unsegmented colored liquid stream circulating in conduit 43 downstream of the second desegmentation means 50 is measured, and the starch content of the substrate analyzed is deduced therefrom.

As a whole, it is noted that operating phases (2) and (3) described above make it possible automatically, by means of the arrangement of FIG. 1, to effect the dispersing of the starch contained in a particulate sample of the substrate to be analyzed, in an aqueous suspension medium. Operating phases (4) and (5) described above make it possible automatically to carry out continuously the operation of enzymatic hydrolysis of the starch dispersion obtained.

Operating phases (9) and (10), possibly preceded by operating phases (6) and (8), which have been described previously, make it possible to carry out automatically and continuously the operation of the preparation of the glucose solution from the hydrolyzed starch dispersion.

In order to be able to have access to the weight content of starch in the different particulate samples of amylaceous substrate treated by means of the automatic determination system described above, it is necessary to have a standard range of different glucose solutions; namely, different glucose concentration standards whose value varies regularly from one standard to another. By way of example, the concentration of the different standards varies uniformly between 20 and 60 micrograms, which corresponds to the zone of the glucose concentrations in which the colorimeter 52 is most sensitive.

One must take into account the coloring conditions used as explained above: As a function of the presumed starch content of the substrate analyzed, adjust the volume of the starch dispersion segment circulating in conduit 19 and/or the volume of the segments of hydrolysis enzymatic preparation mixed with the buffer selected, circulating in conduit 20, possibly and/or the volume of the segments of solvent circulating in conduit 56, and/or the ratio between the cross-sections of conduits 19 and 29, and/or of the conditions of resegmentation, at the location of means 30, and/or the volume of the segments of counter-dialysis solution circulating in conduit 32, in such a manner that the glucose concentration of the segments of glucose solution circulating in conduit 43, at the outlet 42 of the dialysis device 35, is substantially within the aforesaid standard range.

Prior to the determination of the different particulate samples of amylaceous substrate, one must treat each concentration standard in the automatic analysis line represented in FIG. 2; that is to say, introduce each concentration standard through conduit 19, upstream of the peristaltic pump 62'. In this way, each standard sample undergoes, as previously, a segmentation, an addition of a segmented solution of the enzymatic hydrolysis preparation 2 and of buffer 3, a possible addition of a segmented diluent 5, a hydrolysis in the hydrolysis enclosure 24, a desegmentation, a settling, a resegmentation, a dialysis, and an addition of a segmented reactive color solution (6, 7, 8), a desegmentation, and a final titration of the optical density of color in apparatus 52.

Due to the treatment of the standard range, it is possible to establish a calibration curve which makes it possible to obtain the starch content of each substrate analyzed, based on the following formula:

$$a = \frac{X \times V \times 9}{P \times 10^5}$$

in which:
a is the content by weight of starch in the substrate analyzed, expressed in percent of the dry weight of the latter;
X is the glucose concentration, expressed in micrograms/liter, noted on recorder 53, on basis of the calibration curve;

V is the volume of the starch dispersion available in each treatment flask 11 (see FIG. 1), expressed in ml;
P is the weight of the particulate sample (or test sample) dispersed in each treatment flask 11, expressed in grams of dry matter.

By way of example, on the basis of the automatic analysis components presently available on the market, and particularly sized conduits of small cross-section made of compressible, flexible plastic presently marketed, different analytical systems are proposed in Table 1 below and make it possible to obtain substantially close results on recorder 53 for a given total volume of the segments of the mixture to be hydrolyzed, circulating in conduit 19, downstream of the third combination means 59.

TABLE 1

| Ratio between the cross-sections of the different conduits of the analysis line of FIG. 2, and that of | Presumed starch content of the amylaceous substrate analyzed (in weight % of dry matter) | | |
|---|---|---|---|
| | 0 to 15 | 5 to 15 | 15 to 20 |
| conduit 55 | | | |
| conduit 19 | 16 | 8 | 4.2 |
| conduit 56 | — | 9 | 12 |
| conduit 55 | 1 | 1 | 1 |
| conduit 20 | 2.3 | 2.3 | 2.3 |

There should be emphasized the importance of the automatic analysis operating phases (6) to (8) which have been described previously, and therefore the importance of the succession of the desegmentation means 26, the settling means 28, and the resegmentation means 30. As a matter of fact, in the case of complex amylaceous substrates containing other substances than starch—for instance, cellulose proteins, etc.—the large insoluble particles of the hydrolyzed mixture may, on the one hand, at least partially clog the dialysis cell 35 and possibly the colorimetric reaction coil 49 and the colorimeter 52 and, on the other hand, retain, by absorption, a non-negligible part of the glucose resulting from the hydrolysis and therefore modify the dialysis coefficient of the sample analyzed as compared with that of the standard range.

Under these conditions, settling device 28, which, incidentally, could be replaced by a continuous filter, makes it possible to introduce a perfectly clear hydrolysate into the first compartment 37 of hydrolysis cell 35 and therefore to obtain a dialysis coefficient of the glucose coming from the hydrolysis which is substantially close to that of the glucose of the standard range.

The present invention which has just been described has been made possible by the experimental record, the conditions and results of which will now be reported.

We were first of all interested, with the aid of an ultrasonic treatment device which may be similar to that described in FIG. 1, in the conditions for carrying out this dispersion technique, making it possible to obtain results which are not significantly different from those supplied by hydrothermal dispersion (see operating step 2 in accordance with the prior art, described in the Background section).

For this purpose, there was used an ultrasonic generator having an operating frequency of 20 kilocycles and an electric power of 150 W. The concentration and volume conditions (about 0.5 g of particulate sample in 25 ml of ion-exchanged water) which had been used in the manual method of the prior art (see operating step 2 defined in the Background section) were retained in order to compare the manner of dispersion with ultrasonics with that normally employed; namely, "starching" followed by autoclaving. The amount of dispersed starch is determined by conversion into glucose, more precisely by hydrolysis with glucoamylase, and determination of the glucose formed by the glucose-oxydase and the peroxydase, in accordance with operating steps 3 to 5 of the prior art (explained in the Background section). Based on a normal pure cornstarch, it was possible to show, in accordance with Table 2, that it is impossible completely to disperse the starch of an amylaceous substrate by the action of ultrasonics at room temperature.

TABLE 2

| Time of action of ultrasonics in minutes | % by weight of starch dispersed |
|---|---|
| 2 | 33.1 |
| 4 | 32.6 |
| 6 | 35.7 |
| 10 | 31.4 |

These results are verified, whatever the time of action of the ultrasonics and the type of treatment container used, whether it be an Erlenmeyer flask or a test tube. It is therefore found that at room temperature the starch dispersion obtained cannot exceed about 35% of the starch contained in the substrate analyzed.

In the case still of a pure normal cornstarch, if one arranges the ultrasonic treatment Erlenmeyer flask in a boiling water bath, and, therefore, if one maintains the suspension of the particulate sample of pure starch at a temperature of between about 90° C. and about 100° C., it is found—for instance, by observation under an optical microscope—that the dispersion of the particles of starch is complete for a time of action of the ultrasonics of between about 4 and about 6 minutes. This observation is confirmed by Table 3 below, which relates to a pure starch dispersion; on the one hand by hydrothermal treatment, and on the other hand by action of ultrasonics for four minutes at room temperature and at 94° C.

TABLE 3

| | Manual Dispersion "starching" + autoclaving) | Ultrasonics for 4 minutes | |
|---|---|---|---|
| | | Room Temp. | 94° C. |
| No. of samples analyzed | 15 | 12 | 18 |
| Content (in g) of starch per 100 g of pure dry cornstarch | 97.5 ± 1.65 | 33.7 ± 1.7 | 99.3 ± 2.2 |

Preferably, the temperature of dispersion of the particulate samples in the aqueous medium selected is maintained between about 90° C. and about 95° C. As a matter of fact, in general, it is observed that below 90° C. the starch dispersion is insufficient, even if one increases the time of action of the ultrasonics, and it is observed that above 95° C. cavitation phenomena, due to the action of the ultrasonics, take place within the starch dispersion, resulting in a loss of the substance determined.

In the same manner, by systematic tests, it can be stated that the time of action of the ultrasonics should preferably be between about 4 minutes and about 6 minutes. As a matter of fact, it is noted that below 4 minutes the dispersion of starch obtained is insufficient and that above 6 minutes a retrogradation of the treated starch takes place; that is to say, a formulation of new chemical bonds which cannot then be hydrolyzed under the action of the glucoamylase, which obviously impairs the correctness of the determination effected.

To continue, various amylaceous complex substrates were tried out, as indicated in Table 4 below. More precisely, the results obtained (% by weight of starch contained in the dry material of complex substrate analyzed) either by dispersing the starch by the action of ultrasonics or by dispersing the starch in a conventional matter; that is to say, by a hydrothermal treatment.

TABLE 4

| | Method of dispersing | |
|---|---|---|
| | Ultrasonics | "Starching" + Autoclaving |
| Rice starch | 98.5 | 96.9 |
| Casava starch | 98.3 | 97.2 |
| Normal corn meal | 80.7 | 81.5 |
| Waxy corn meal | 82.8 | 84.4 |
| Extruded corn meal | 81.3 | 82.4 |
| Rice meal | 93.8 | 91.1 |
| Oats | 42.8 | 42.6 |
| Millet flour | 79.7 | 79.4 |
| Field bean (16 samples) | 35.5 ± 3.3 | 36.0 ± 3.7 |

The results set forth in the above table show that the conditions of dispersion of the starch under the action of ultrasonics which have been previously defined are satisfactory for all the complex amalaceous substrates studied. A statistical comparison of the results obtained, by the method of pairs, makes it possible to note that the two methods of dispersion—namely, the conventional method and the method in accordance with the invention—give results which are not statistically different. The same statistical comparison, effected on the 16 samples of beans studied, makes it possible to arrive at the same conclusion. As a whole, for a given particulate sample, the reproducibility of the results is substantially the same, since the coefficient of variation is between 1 and 3% for the two methods used.

However, in the case of starches having a physical-chemical structure which is particularly resistant to dispersion—for instance, in the case of starches which are rich in amylose—it is advisable to add a dispersing agent to the aqueous dispersion medium in order to favor and increase the dispersing action of ultrasonics. In this connection, among all the chemical dispersion agents used at the present time, preference is to be given to chloralhydrate or 2,2,2,-trichloro-1,1-ethanediol, which has proved to be a product having the best performance with respect to the dispersion sought. Furthermore, it has been found that chloralhydrate does not exert any influence on the enzymatic activity of the glucoamylase during the hydrolysis of the dispersed starch, or of the glucose oxydase and peroxydase during the determination of the glucose resulting from the hydrolysis.

In conclusion, ultrasonics can be substituted for "starching" followed by autoclaving in order to disperse the starch of a particulate sample in a suitable aqueous medium, but provided that all or part of the operating parameters defined above are utilized. Only the latter make it possible to disperse the starch sufficiently in order that the subsequent enzymatic hydrolysis will be complete, but also in a manner which is not so extensive that the particulate substrate treated is transformed beyond the glucose state, which constitutes the end product serving for the determination of the starch content.

Then we concerned ourselves with the determination of the operating conditions which permit the automatic determination of starch with the automatic analysis line described in FIGS. 2 and 2a to 2c.

For this purpose, the operating conditions selected must take into account the following factors which are related to the automatic analysis line selected, which has been shown in FIG. 2:

Factor 1: Taking into account the characteristics of the peristaltic proportioning pumps now on the market and on the basis of the sized conduits of compressible, flexible plastic material at present on the market, the latter must have a maximum ratio and a minimum ratio of cross-sections between each other in order that they can be used jointly on the same peristaltic pump. Consequently, the ratios between the different reagents must not only satisfy the operating conditions selected for the enzymatic hydrolysis of the starch and the colorimetric and enzymatic determination of the glucose, but they must also be within the range of ratios established for the sized conduits, at the location of the peristaltic pump 62'.

Factor 2: In view of the smallness of the volume of the different segments—on the one hand, of the mixture to be hydrolyzed circulating in conduit 19, and on the other hand, of the glucose solution circulating in conduit 43—the ratios of the different reagents, and particularly the enzyme/amylaceous substrate weight ratio must be adapted to these new conditions of determination, as a function of the possibilities of the automatic analysis line selected.

Factor 3: In order that the automatic analysis line of FIG. 2 can be suitably used in practice, it is necessary that the hydrolysis time—that is to say, the time of recirculation in coil 25 of the starch dispersion and the enzymatic hydrolysis preparation—is not too long.

Factor 4: In view of the fact that it is no longer possible to effect, in the dialysis cell 35, a washing of the solid residue of the hydrolyzed mixture, the dilution of the hydrolysate must be suitably selected in such a manner that the dialysis employed is equivalent to the filtration followed by washing which is used in the prior art (see operating step 4 in the Background section).

Factor 5: In view of the continuous character of the automatic analysis line shown in FIG. 2, it is necessary that the reagents and the operating conditions selected do not cause any harmful interference between, on the one hand, the enzymatic hydrolysis of the starch, and, on the other hand, the enzymatic and colorimetric determination of the glucose, since the hydrolysis reagents, in particular, are found again in part upon the colorimetric determination of the glucose.

Factor 6: As in any colorimetric determination, whether manual or automatic, it is neccesary finally to select the concentration of the different reagents in such a manner that the colorimetrically determined stream has a glucose concentration which is comparable with the limits of sensitivity of the colorimeter.

All the results set forth below were obtained from a starch dispersion, whether a simple or complex amylaceous substrate, by starching and autoclaving.

With respect to the weight ratio of the enzymatic hydrolysis preparation contained in a segment of the mixture of the starch dispersion and the enzymatic preparation in question, circulating in conduit 19—for instance, at the entrance to hydrolysis enclosure 24—with respect to the weight of the particulate sample of the substrate analyzed contained in the same segment of the same mixture, it has been possible to establish that it should be considerably increased with respect to the ratio (between about 10 and 20% used in accordance with the manual method of the prior art, and preferably be between 4 and 10, in view of the following factors:

(1) For a minimum flow of the enzymatic hydrolysis preparation 2 circulating in the conduit 20 of FIG. 2, it would have been necessary to use a conduit 19 (see FIG. 2) whose cross-section, with respect to that of conduit 20, would exceed the maximum ratio to be specified for the different conduits connected with peristaltic pump 62', if one holds to the enzyme/substrate ratio used in the prior art. It was therefore decided to retain a normal size for conduit 19 of FIG. 2 and, corresponding to this, it was decided to increase the size of conduit 20, which then leads to increasing the aforesaid enzyme/substrate ratio beyond the values of the prior art.

(2) However, this enzyme/substrate ratio must not be too high, since, starting at a ratio greater than about 10, it has been possible to establish that the hydrolysis then became incomplete, this being undoubtedly due to an inhibiting of the hydrolysis reaction of the starch or of the enzymatic and colorimetric determination of the glucose by an excess of the components of the enzymatic hydrolysis preparation. However, the enzyme/substrate ratio selected must be sufficiently large to lead to a complete hydrolysis of the starch. In this respect, it has been established that the ratio has to be at least equal to about 4. The enzyme/substrate ratio is preferably equal to about 7.

With respect to the hydrolysis time—that is to say, the period of time during which the segmented flow of the mixture of the starch dispersion and the enzymatic hydrolysis preparation circulates in hydrolysis enclosure 24—based on different amylaceous substrates, it was possible to note that the transformation of the starch into glucose is practically complete at the end of 30 minutes. It is deduced from this that the hydrolysis time can be substantially reduced as compared with the time employed in the prior art, without, however, being less than 30 minutes.

Due to the numerous experiments carried out, it can be stated that the hydrolysis time should preferably be between about 60 minutes and about 90 minutes. And it can be stated that this period of operation is sufficient to assure complete degradation of the starch, whatever its physical-chemical structure, and therefore whatever the amylaceous substrate treated, with the exception of those complex substrates which are well known to those skilled in the art as being particularly resistant to dispersion; for instance, amylaceous substrates which are rich is amylose.

The experimentation carried out has, in particular, shown that it was not advisable to increase the hydrolysis time beyond 90 minutes, since one then arrives at the formation of a deposit in the circulation conduits of the analysis line of FIG. 2 and more precisely within coil 25, which results in the necessity of excessively frequent cleaning of the entire analytical line, which is incompatible with the saving in time sought.

With respect to the influence of the conditions of hydrolysis on the calibration curve, it will be recalled that, in one method of operation in accordance with the invention which has been defined previously, the standard glucose range undergoes the same treatment, in the automatic determination line of FIG. 2, as the different samples analyzed. This operating method is different from that employed in accordance with the prior art since, in accordance with the prior manual method, the standard range does not undergo hydrolysis before colorimetric treatment.

It would therefore by necessary to verify that the values supplied by the standard range, in the case of an automatic analysis in accordance with the invention, were similar to those obtained in accordance with the prior art; that is to say, in accordance with the manual method. For this purpose, a standard range of glucose was hydrolyzed for two hours on a water bath at 55° C. with constant agitation; that is to say, under the same conditions of hydrolysis as those described for the method of determination in accordance with the prior art (see operating step 3 in the Background section). The optical densities obtained for the different standards of glucose solutions are identical, whether the standards in question underwent the hydrolysis defined previously or not. Therefore, in accordance with the invention, it is entirely possible to introduce the standard range at the same point as the starch dispersions; that is to say, at the inlet of conduit 19 in FIG. 2.

With respect to the influence of the bactericidal agent used in accordance with the prior art (for instance, sodium merthiolate) which makes it possible to prevent the development of microbic agents which might degrade the glucose during the period of a few hours to a few days between the enzymatic hydrolysis and enzymatic determination of the glucose, it has been possible to establish experimentally that this agent caused an inhibiting of the coloring reaction serving for the determination of the glucose, so that there was a substantial decrease in the sensitivity of the starch determination. After having verified on different samples of amylaceous substrates determined in accordance with the method of the prior art—that is to say, manually—that the bactericidal agent used (for instance, merthiolate), had no influence on the yield of the hydrolysis of starch into glucose, the agent in question was then eliminated. This therefore means that in accordance with the present invention, the segmented flow of the mixture of the dispersion of starch and of the enzymatic hydrolysis preparation circulating in conduit 19 of FIG. 2 no longer includes any bactericidal agent.

With respect to the particle size of the particulate sampled treated, on the basis of numerous experiments, it has been shown that it should be equal at most of 0.4 mm, in order to obtain results which are not significantly different from those obtained by the method of the prior art; that is to say, the manual method.

The operating conditions which characterize the present invention and therefore the automatic method for the determination of starch previously described, having been determined experimentally, as reported above, the automatic process of the invention was then applied, on the one hand, to simple amylaceous substrates which were very rich in starch in accordance with Table 5, and, on the other hand, to complex amylaceous substrates, in accordance with Table 6. In each case, the results obtained in accordance with the invention were compared with those obtained in the prior art, in accordance with the manual method explained in the preamble to the present specification.

TABLE 5

| | Analysis number | Automatic method in accordance with the invention | Manual method in accordance with the prior art |
|---|---|---|---|
| | | α | α |
| Cornstarch | 8 | 97.26 ± 1.02 | 97.20 ± 1.17 |
| | | β | β |
| Potato starch | 8 | 99.89 ± 1.43 | 100.52 ± 1.50 |
| Rice starch | 2 | 97.20 | 95.30 |
| Wheat starch | 2 | 96.45 | 95.80 |
| Average of all the samples | 20 | 98.23 c | 98.20 c |

Remarks:
The numbers provided with the same superscript letter on the same line are not significantly different.
The standard analysis of the results could not be effected on the samples of rice starch and wheat starch, in view of the small number of samples determined.

TABLE 6

| | Automatic method according to the invention | Manual method according to the prior art |
|---|---|---|
| Rye | 67,00 ± 1,16 | 65,50 ± 0,17 |
| Hard wheat | 67,28 ± 0,03 | 68.03 ± 0,12 |
| Soft wheat (not screened) | 62,96 ± 0,03 | 63,67 ± 0,86 |
| Soft wheat (screened) | 67,18 ± 2,57 | 65,90 ± 0,72 |
| Barley clothed | 62,20 ± 1,31 | 61,29 ± 0,90 |
| Barley clothed | 63,86 ± 0,51 | 63,32 ± 0,91 |
| Barley clothed | 59,04 ± 1,20 | 58,56 ± 2,34 |
| Barley bare | 67,44 ± 0,78 | 65,28 ± 0,68 |
| Oats bare | 63,43 ± 0,64 | 62,05 ± 0,47 |
| Corn | 69,70 ± 1,52 | 71,05 ± 1,36 |
| Corn opaque 2 | 58,83 ± 1,94 | 63,99 ± 0,44 |
| Corn opaque 2 | 62,11 ± 0,77 | 65,03 ± 1,43 |
| Corn waxy | 68,62 ± 0,13 | 69,31 ±0,04 |
| Sorghum | 62,86 ± 1,45 | 66,10 ± 2,19 |
| Triticale | 64,79 ± 0,64 | 60,80 ± 1,93 |
| Field bean | 39,98 ± 0,94 | 40,35 ± 0,98 |
| Peas | 44,33 ± 1,63 | 44,67 ± 0,06 |
| Casaba flour | 76,53 ± 1,30 | 78,43 ± 0,52 |
| Banana flour | 80,99 ± 0,99 | 79,06 ± 0,00 |
| Sweet potato flour | 73,28 ± 0,65 | 72,49 ± 0,08 |
| Cattle feed | 51,20 ± 0,08 | 49.93 ± 0,58 |

Remark:
The determinations were repeated a maximum of 6 times for each sample.

The analytical results set forth in Tables 5 and 6 are understood in % by weight starch of the dry matter of the substrate analyzed. The validity of the operating principles in accordance with the invention is then shown, as a function of the following observations:

(1) With respect to the substantially pure starches (see Table 5), the correspondence between the automatic method in accordance with the invention and the manual method in accordance with the prior art is excellent, both for all of the substrates studied (20 experimental results) and for all of the substrates (corn and potato starches) determined in a number sufficiently large (8) in order to be able to effect a statistical analysis of the results. In all cases, the differences observed remain small and are never significant. The reproducibility of the determination, by the manual method or the automatic method, is substantially the same; the coefficient of variation, calculated on 8 samples, is very close, whatever the sample analyzed (1.04 and 1.20 for cornstarch; 1.43 and 1.49 for potato starch).

(2) With respect to the complex amylaceous substrates (see Table 6), the results obtained are, as a whole, very satifactory. The differences observed between the automatic method of the invention and the manual method of the prior art are not significant either for the total of 21 different samples of amylaceous products determined or for the different classes of foods studied (namely—first, of all 15 grains; secondly, two legume seeds; thirdly, three flours of amylaceous products; and fourthly, a cattle feed). The reproducibility of the automatic method is comparable to that of the manual method; the mean coefficient of variation calculated on the total results is 1.49% and 1.31%, respectively; only a few differences are observed in the case of the starches whose physical-chemical nature is particularly resistant to dispersion (sorghum and opaque corn 2). In conclusion, it would appear that, for almost all of the amylaceous products available in practice, the automating of the enzymatic hydrolysis gives results comparable to those obtained by the manual method of the prior art.

While there have been shown preferred methods and systems for starch determination in accordance with the invention, it will be appreciated that many changes and modifications may be made therein without, however, departing from the essential spirit thereof.

We claim:

1. The method of analyzing a series of substrates containing starch to determine the weight of the starch in each substrate therein, said method comprising the steps of:
    A. suspending a sample of each substrate in particulate form in an aqueous medium to disperse said starch to produce a series of samples to be tested;
    B. hydrolyzing the starch dispersion of each sample with an enzymatic hydrolysis preparation containing glucoamylase to convert the dispersed starch into glucose dissolved in the aqueous medium to obtain a hydrolysate, the hydrolyzing step carried out continuously by (1) forming a segmented flow, each segment of which is a mixture of a respective sample of the starch dispersion in the series thereof and the hydrolysis preparation, the segmented flow being constituted by the series of mixture segments isolated by gas-filled gaps which segregate the segments from each other, and (2) causing the segmented flow thus formed to circulate in a hydrolysis enclosure for a period sufficient to convert the dispersed starch in the aqueous medium in each of said mixture segments into glucose dissolved in said aqueous medium to produce a hydrolysate;
    C. preparing a glucose solution from the hydrolysate obtained in each of said segments which contains at least a predetermined part of the glucose resulting from the hydrolysis; and
    D. determining the weight of the glucose in said glucose solution to deduce therefrom the weight content of the starch in each substrate of said series thereof.

2. The method as set forth in claim 1, wherein the step of preparing said glucose solution is carried out by:
    A. forming a first segmented flow of said hydrolysate, constituted by a series of hydrolysate segments isolated from each other by gas-filled gaps;
    B. forming a second segmented flow of a counter-dialysis solution constituted by a series of counter-dialysis solution segments isolated from each other by gas-filled gaps; and
    C. causing the first segmented flow and the second segmented flow to circulate in the same direction on opposite sides of a dialysis wall, such that by at least partial diffusion of glucose from a hydrolysate segment toward a segment of the counter-dialysis solution, one obtains, on the one hand, a segmented flow of the hydrolysate which is at least partially exhausted in glucose, and, on the other hand, a segmented flow of a glucose solution.

3. The method as set forth in claim 2, further characterized by the fact that the segmented flow of hydrolysate is obtained continuously from the segmented flow of the hydrolyzed mixture of the starch dispersion and the enzymatic hydrolysis preparation by:
    A. desegmenting the segmented flow of the hydrolyzed mixture to break it down into a gaseous stream formed of the different gas-filled gaps and into a non-segmented stream of the hydrolyzed mixture formed of the different segments thereof;
    B. separating from the non-segmented stream of hydrolyzed mixture thus obtained, relatively fine particles of the insoluble residue which is insoluble in the aqueous medium of the hydrolyzed mixture by dividing said non-segmented stream into a first non-segmented flow containing said relatively fine particles and a second non-segmented flow containing the relatively coarse particles of said solid residue; and
    C. resegmenting the flow of the hydrolysate by reforming from the first non-segmented flow and from the gaseous stream, a segmented flow constituted by segments of the hydrolysate isolated from each other by gas-filled gaps.

4. The method as set forth in claim 3, further characterized by the fact that the relatively fine particles are separated by gravity from the relatively coarse particles of the solid residue which is insoluble in the aqueous medium of the hydrolyzed mixture.

5. The method as set forth in claim 1, further characterized by the fact that dispersion of the starch in said aqueous medium is effected by ultrasonically agitating the particulate sample suspension in said aqueous medium while maintaining the suspension at a temperature of between about 90° to 95° C.

6. The method as set forth in claim 1, further characterized by the fact that the segmented flow of the mixture of the starch dispersion and of the enzymatic hydrolysis preparation is maintained free of any bactericidal agent.

7. The method as set forth in claim 1, further characterized by the fact that the hydrolysis period during which the segmented flow of the mixture of the starch dispersion and of the enzymatic hydrolysis preparation circulates in the hydrolysis enclosure runs at least about 30 minutes.

8. The method as set forth in claim 7, further characterized by the fact that the hydrolysis period runs between about 60 minutes and about 90 minutes.

9. The method as set forth in claim 1, further characterized by the fact that the particle diameter of the substrate sample is at most equal to 0.4 mm.

10. The method as set forth in claim 5, further characterized by the fact that the ultrasonic agitation is carried out for about 4 to 6 minutes.

11. The method as set forth in claim 1, further characterized by the fact that the weight ratio of the enzymatic hydrolysis preparation contained in a segment of the mixture of the starch dispersion and the enzymatic preparation relative to the weight of the particulate sample of the substrate contained in the same segment of said mixture is between about 4 and 10.

12. A method as set forth in claim 5, further characterized by the fact that the dispersion of starch is effected in the presence of a chemical dispersing agent.

* * * * *

UNITED STATES PATENT OFFICE
CERTIFICATE OF CORRECTION

Patent No. 4,188,466   Dated February 12, 1980

Inventor(s) Pierre Thivend, et al

It is certified that error appears in the above-identified patent and that said Letters Patent are hereby corrected as shown below:

Column 2, line 6 "50°0" should have read -- 50° --

Column 14, line 38 "of" third occurrence should have read -- in --

Column 18, line 11 "matter" should have read -- manner --

Column 20, line 55 "is" should have read -- in --

Column 21, line 7 "by" should have read -- be --

Signed and Sealed this

Twenty-eighth Day of October 1980

[SEAL]

Attest:

SIDNEY A. DIAMOND

Attesting Officer

Commissioner of Patents and Trademarks